US009471976B2

(12) United States Patent
Thiruvenkadam et al.

(10) Patent No.: US 9,471,976 B2
(45) Date of Patent: Oct. 18, 2016

(54) SYSTEM AND METHOD FOR DATA DRIVEN GATING OF MULTIPLE BED POSITIONS

(71) Applicants: General Electric Company, Schenectady, NY (US); King's College London, London (GB)

(72) Inventors: Sheshadri Thiruvenkadam, Bangalore (IN); Krishna Seetharam Shriram, Bangalore (IN); Ravindra Mohan Manjeshwar, Glenville, NY (US); Srikrishnan Viswanathan, Bangalore (IN); Kris Filip Johan Jules Thielemans, London (GB)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 14/626,976

(22) Filed: Feb. 20, 2015

(65) Prior Publication Data

US 2016/0247274 A1      Aug. 25, 2016

(51) Int. Cl.
*G06K 9/00* (2006.01)
*G06T 7/00* (2006.01)
*G06T 7/20* (2006.01)

(52) U.S. Cl.
CPC .............. *G06T 7/0012* (2013.01); *G06T 7/20* (2013.01)

(58) Field of Classification Search
None
See application file for complete search history.

(56) References Cited

U.S. PATENT DOCUMENTS

| | | |
|---|---|---|
| 6,408,107 B1 | 6/2002 | Miller et al. |
| 2005/0123183 A1 | 6/2005 | Schleyer et al. |
| 2006/0178575 A1 | 8/2006 | Piacsek et al. |
| 2008/0226149 A1* | 9/2008 | Wischmann ............ A61B 6/503 382/131 |
| 2010/0067765 A1 | 3/2010 | Buther et al. |
| 2010/0220909 A1* | 9/2010 | Thielemans .......... G06T 11/005 382/131 |
| 2012/0014501 A1* | 1/2012 | Pelc ...................... A61B 6/025 378/9 |
| 2012/0281897 A1 | 11/2012 | Razifar et al. |
| 2012/0305780 A1 | 12/2012 | Thiruvenkadam et al. |
| 2013/0035588 A1* | 2/2013 | Shea .................. G01R 33/4833 600/413 |
| 2013/0070994 A1* | 3/2013 | Liang .................... G06T 11/006 382/131 |
| 2015/0289832 A1* | 10/2015 | Bal ...................... A61B 6/5264 600/411 |

OTHER PUBLICATIONS

Thireou et al., "Performance Evaluation of Principal Component Analysis in Dynamic FDG-PET Studies of Recurrent Colorectal Cancer", Computerized Medical Imaging and Graphics , pp. 43-51, vol. 27, 2003.

(Continued)

*Primary Examiner* — Bhavesh Mehta
*Assistant Examiner* — Oneal R Mistry
(74) *Attorney, Agent, or Firm* — Melissa K. Dobson

(57) ABSTRACT

A method implemented using at least one processor includes receiving time-varying image dataset generated by a medical imaging modality. The image dataset corresponds to a bed position and is affected by quasi-periodic motion data. The method also includes applying a signal decomposition technique to the time-varying image dataset to generate a plurality of dataset components and a plurality of motion signals. The method also includes determining reference data based on the time-varying image dataset, wherein the reference data is representative of a direction of the quasi-periodic motion. The method further includes deriving polarity of each of the plurality of motion signals based on the reference data to generate a plurality of sign corrected motion signals. The method also includes determining a gating signal corresponding to the bed position based on at least one of the plurality of sign corrected motion signals.

16 Claims, 5 Drawing Sheets

(56) References Cited

OTHER PUBLICATIONS

Alessio et al., "Consistency Driven Respiratory Phase Alignment and Motion Compensation in PET/CT", IEEE Nuclear Science Symposium Conference Record, pp. 3115-3119, 2007.

Georg et al. "Manifold learning for 4D CT reconstruction of the lung," Computer Vision and Pattern Recognition Workshops, CVPRW '08. IEEE Computer Society Conference on, Jun. 2008, 10 Pages.

Schleyer et al., "Retrospective Data-Driven Respiratory Gating for PET/CT", Physics in Medicine and Biology, vol. 54, Issue 7, pp. 1935-1950, 2009.

Schleyer et al., "Extension of a data-driven gating technique to 3D, whole body PET studies", Physics in Medicine and Biology, vol. 56, Issue 11, pp. 3953-3965, 2011.

Authors et. al.: Disclosed Anonymously, "Refinement of Data Driven Gating Baesd on Analysis of Derived Motion Charecteristics", IP.com, An IP.com Prior Art Database Technical Disclosure, Jul. 17, 2013, 8 Pages.

Schleyer et al., "Comparing Approaches to Correct for Respiratory Motion in NH3 PET-CT Cardiac Perfusion Imaging", Nuclear Medicine Communications, pp. 1174-1184, vol. 34, Issue 12, Dec. 2013.

\* cited by examiner

SYSTEM AND METHOD FOR DATA DRIVEN GATING OF MULTIPLE BED POSITIONS

BACKGROUND

A system and method are disclosed for generating a gating signal for Positron Emission Tomographic (PET) data. Specifically, the system and method are related to generating a data driven gating signal for PET data acquired from multiple bed positions.

Medical imaging systems use non-invasive techniques to image and visualize internal structures and/or functional behavior of organs of a patient. Medical imaging systems are based on ultrasound, computed tomography (CT), x-ray, positron emission tomography (PET), single photon emission computed tomography (SPECT), and magnetic resonance (MR) techniques.

PET images from a patient are acquired over a time interval of several minutes for diagnosis, radiation therapy (RT) and radiation therapy planning (RTP). During the acquisition, patient movements due to respiration activity, cardiac activity and other gross patient movements results in noise signals. The noise signals generate blurring of the generated images, consequently resulting in wrong diagnosis and therapeutic decisions.

Conventionally, gating techniques are employed to mitigate the effects of respiration and cardiac motion on the PET data. A respiratory or cardiac motion signal acquired during the acquisition of the PET data, is used to identify portions of the PET data having similar phase of the quasi-periodic patient movements. Identified portions of PET data are used to determine motion free PET data. However, gated signals suffer from a low signal-to-noise ratio due to reduced photon counts recorded within a corresponding acquisition time interval. Image registration required for reducing the effects of motion data, use of independently acquired respiratory or cardiac data limit the quality of the gating signal generated through this technique.

Data driven gating is a class of techniques used to determine the respiratory and/or cardiac motion based on the acquired PET dataset. The acquired data is analyzed and a gating signal is generated for identifying data in a plurality of (for instance respiratory) motion states. Some data driven methods however generate a signal that is of arbitrary scale and sign. This can be problematic in certain applications where it is necessary to distinguish between e.g. inspiration and expiration, or diastole and systole. This is also the case for PET data acquired from multiple bed positions as this introduces the additional requirement of stitching the gating signal across the bed positions.

It is therefore desirable to develop a system and method for generating a gating signal from PET data with a fixed sign, especially for data acquired from multiple bed positions.

BRIEF DESCRIPTION

One example of a method disclosed, comprises receiving time-varying image dataset corresponding to a bed position, wherein the time-varying image dataset is generated by a medical imaging modality and affected by quasi-periodic motion data. The method also includes applying a signal decomposition technique to the time-varying image dataset to generate a transformed dataset, wherein the transformed dataset comprises a plurality of dataset components and a plurality of motion signals. The method also includes determining a reference data based on the time-varying image dataset, wherein the reference data is representative of a direction of the quasi-periodic motion. The method further includes deriving polarity of each of the plurality of motion signals based on the reference data to generate a plurality of sign corrected motion signals. The method also includes determining a gating signal corresponding to the bed position based on at least one of the plurality of sign corrected motion signals.

One embodiment of a system comprises at least one processor module and a memory module communicatively coupled to a communications bus. The system also includes a pre-processor module receiving time-varying image dataset corresponding to a bed position, wherein the time-varying image dataset is generated by a medical imaging modality and affected by quasi-periodic motion data. The system also includes a motion signal generator module communicatively coupled to the pre-processor module and configured to perform signal decomposition of the time-varying image dataset and generate transformed dataset, wherein the transformed dataset comprises a plurality of dataset components and a plurality of motion signals. The system also includes a motion signal analysis module communicatively coupled to the motion signal generator module and configured to determine a reference data based on the time-varying image dataset, wherein the reference data is representative of a direction of the quasi-periodic motion. The motion signal analysis module is also configured to derive polarity of each of the plurality of motion signals based on the reference data and the transformed dataset to generate a plurality of sign corrected motion signals. The motion signal analysis module is further configured to determine a gating signal corresponding to the bed position based on at least one of the plurality of sign corrected motion signals. In the system, at least one of the pre-processing module, the motion signal generator module, the motion signal analysis module are stored in the memory module and executable by the processor module.

A non-transitory computer readable medium having instructions is also disclosed. The instructions enable at least one processor to receive time-varying image dataset corresponding to a bed position, wherein the time-varying image dataset is generated by a medical imaging modality and affected by quasi-periodic motion data. The instructions also enable at least one processor to apply a signal decomposition technique to the time-varying image dataset to generate a transformed dataset, wherein the transformed dataset comprises a plurality of dataset components and a plurality of motion signals. The instructions also enable the processor to determine a reference data based on the time-varying image dataset, wherein the reference data is representative of a direction of the quasi-periodic motion. The instructions further enable the processor to determine a gating signal corresponding to the bed position based on at least one of the plurality of sign corrected motion signals.

DRAWINGS

These and other features and aspects of embodiments of the invention will become better understood when the following detailed description is read with reference to the accompanying drawings in which like characters represent like parts throughout the drawings, wherein.

DETAILED DESCRIPTION

Embodiments of methods and systems generate gating signals for a time-varying image dataset that is acquired from a bed position, and determine quasi-periodic motion data based on the time-varying image dataset. A plurality of dataset components and a plurality of motion signals corresponding to the time-varying image dataset are determined based on a signal decomposition technique. At least one motion signal, among the plurality of motion signals corresponding to at least one dataset component among the plurality of dataset components, is selected. The polarity of the selected motion signals is determined based on reference data representative of patient motion. A gating signal corresponding to the bed position is determined based on at least one motion signal and the corresponding polarity. The embodiments further comprise determining a plurality of gating signals corresponding to a plurality of bed positions and a plurality of imaging modalities.

The term time-varying image dataset refers to unlisted four dimensional image data acquired from an imaging system employing one or more imaging techniques such as PET, SPECT, CT or MR. The term bed position refers to a stationary position of the patient while the images are acquired. The term quasi-periodic motion data refers to signals representative of respiratory or cardiac motion or any other quasi-periodic motion associated with the patient within the duration of one bed position. The term dataset component refers to a component of the time-varying dataset such as a basis vector corresponding to the time-varying image dataset. The term motion signal refers to a projection of the time-varying image dataset onto the dataset components determined by a decomposition technique. The term gating signal refers to an estimate of the quasi-periodic motion data determined based on the acquired time-varying image dataset. The terms 'processor' and 'memory' are used interchangeably with the terms 'processor module' and 'memory module' respectively. The terms 'sign', and 'polarity' are used equivalently and interchangeably referring to the relative phase of one signal with reference to another signal.

Figure 1:
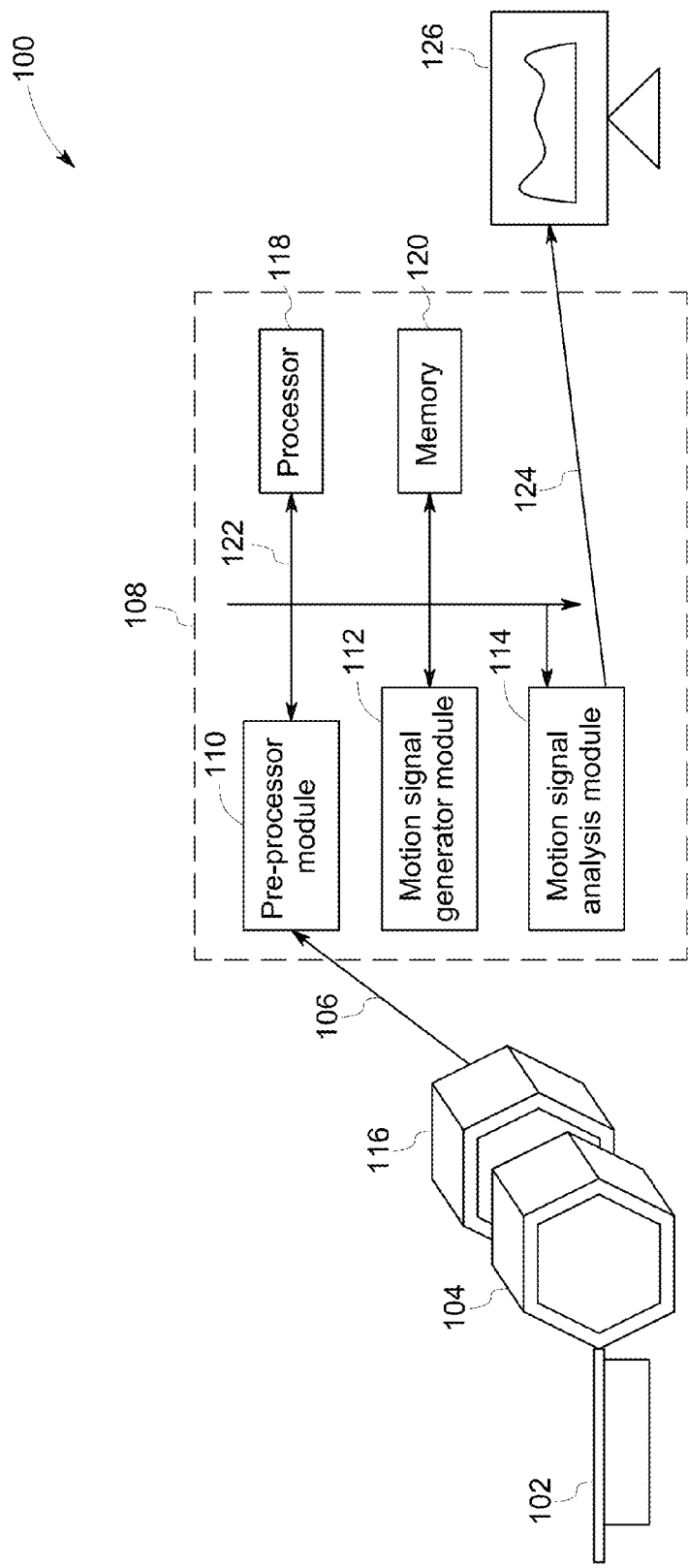
FIG. 1 is a diagram of an embodiment of a system for determining a gating signal for a multi bed position.

FIG. 1 is a diagram of an imaging system 100 for determining a gating signal for a multi bed position in accordance with an exemplary embodiment. The imaging system 100 includes a patient table 102 receivable by at least one of imaging modalities 104 and 116 generating a time-varying image dataset 106. The imaging modality 104 in one embodiment is a positron emission tomographic (PET) system. The imaging modality 116 is a computer tomographic (CT) system. In another embodiment, the imaging modality 116 is a magnetic resonance (MR) system. A gating system 108 is communicatively coupled to the imaging modalities 104 and 116 and configured to receive the time-varying image dataset 106. The gating system 108 generates a gating signal 124 corresponding to the time-varying image dataset. In one embodiment, the gating system 108 generates a gated image dataset based on the time-varying image dataset 106 and the gating signal 124. In the illustrated embodiment, the gating system 108 is communicatively coupled to a computer display device 126.

The gating system 108 includes a pre-processor module 110, a motion signal generator module 112, a motion signal analysis module 114, a processor module 118, and a memory module 120. The modules 110, 112, 114, 118, and 120 are communicatively coupled to each other through a communications bus 122.

The pre-processor module 110 is communicatively coupled to the imaging modality 104 and is configured to receive the image dataset 106 corresponding to a bed position. The time-varying image dataset generated by a medical imaging modality 104, is affected by quasi-periodic motion data. In one embodiment, the time-varying image dataset 106 corresponds to a list mode image dataset and the pre-processor module 110 converts the list mode three dimensional (3D) image dataset to a four dimensional (4D) image data indexed by time. In another embodiment, the time-varying image dataset 106 is a 4D image dataset provided by the imaging modality 104. In general, the pre-processor module 110 is configured to receive data from multiple bed positions. In one embodiment, the image dataset includes data from a plurality of bed positions. The time-varying image dataset may further include data from a plurality of imaging modalities 104 and 116, and a plurality of bed positions. In one embodiment, the time-varying dataset corresponds to a PET-CT system having six bed positions. In another embodiment, the time-varying dataset corresponds to a PET-MR system having eight bed positions.

The motion signal generator module 112 is communicatively coupled to the pre-processor module and configured to generate a transformed dataset by applying a signal decomposition technique to the time-varying dataset. The signal decomposition technique is applied to the time-varying image dataset corresponding to the bed position. The transformed dataset includes a plurality of dataset components and a plurality of motion signals corresponding to the plurality of dataset components. In one embodiment, the plurality of dataset components are generated based on principal component analysis (PCA) of the time-varying image dataset. In another embodiment, an independent composition analysis (ICA) of the time-varying image dataset is performed to generate a plurality of independent components as the plurality of dataset components. The plurality of dataset components may be any basis functions for the time-varying image dataset. In the context of PCA, the plurality of dataset components are also referred to as the plurality of singular vectors (also sometimes called "principal components"). For PCA, the time-varying image dataset at each time instant may be expressed as a linear combination of the plurality of dataset components.

The motion signal generator module 112 is configured to determine a plurality of motion signals corresponding to the plurality of dataset components based on the time-varying image dataset. The plurality of motion signals are generated by projecting the time-varying image dataset onto the plurality of dataset components. In one embodiment, each of the motion signals is a projection of the time-varying image dataset with a dataset component among the plurality of dataset components. In one embodiment, the projection can be an inner product which may be determined as a matrix multiplication. In the case of PCA, the motion signal for each singular vector corresponds to the weight of that singular vector at each time instant in the linear combination of the plurality of dataset components. As the singular vectors are orthogonal by construction when using PCA, this weight can be computed by the inner product of the singular vector and the original data (shifted to zero mean over time) at that time instant.

The motion signal analysis module 114 is communicatively coupled to the motion signal generator module 112 and configured to select at least one motion signal among the plurality of motion signals corresponding to at least one dataset component among the plurality of dataset components based on the quasi-periodic motion data. In one embodiment, the motion signal analysis module 114 is configured to select one or more motion signals having frequency components overlapping with the frequency components of the quasi-periodic motion data. In other embodiment, the motion signal analysis module 114 is configured to select at least one motion signal correlated with the quasi-periodical motion data.

In an exemplary embodiment involving PET data, the motion signals having frequency spectrum in the respiratory frequency range of from 0.1 Hz to 0.4 Hz are selected. In another exemplary embodiment involving CT data, the motion signals that are correlated with the lung density signals corresponding to the bed position are selected. In some embodiments, only one motion signal is selected for representing the respiratory data or lung density signal. In another embodiment, more than one motion signal are selected for representing the quasi-periodic motion data. In some embodiments, other signals, for example, representative of lung extent, tissue volume, and background volume may be considered for selecting the motion signals.

The motion signal analysis module 114 is further configured to determine reference data for selecting at least one dataset component among the plurality of dataset components and determining polarity of the selected motion signal. In one embodiment, the reference data is a reference image, determined based on the time-varying image dataset. A mean image of the plurality of images of the time-varying image dataset is determined. The mean image is shifted in a known predetermined direction to generate a shifted mean image. The reference image is determined as a difference between the mean image and the shifted mean image. The reference image is correlated with each of the dataset components of the time-varying image dataset representative of the motion signals to generate a plurality of cross correlation coefficients. The sign of each of the cross correlation coefficients is used to determine the polarity of the corresponding motion signal. A positive value of a cross correlation coefficient is indicative of phase alignment of corresponding motion signal with known predetermined direction of motion. In such a case, the sign of the corresponding motion signal is not changed. A negative value of the cross correlation coefficient is indicative of phase reversal of the corresponding motion signal with known predetermined direction of motion. In such a case, the sign of the corresponding motion signal is changed. The motion signal analysis module 114 generates a plurality of sign corrected motion signals which are phase aligned with the motion data. The motion signal analysis module 114 is also configured to determine a gating signal corresponding to the bed position based on the sign corrected motion signals.

In one embodiment, the time-varying image dataset includes data from a plurality of bed positions. In such a case, a plurality of gating signals are generated corresponding to each of the bed positions. A gated image dataset is generated from the time-varying image dataset using the plurality of gating signals. The gated image dataset includes a plurality of gated image datasets corresponding to the plurality of bed positions. The plurality of gated image datasets are combined to generate a combined dataset. In one embodiment, the plurality of bed positions partially overlap. In a specific embodiment, the combination step takes this overlap into account during the image reconstruction stage to generate a plurality of gated images where all bed positions are merged.

The processor 118 is communicatively coupled to the communications bus 122 and includes at least one arithmetic logic unit, a microprocessor, a general purpose controller or a processor array to perform the desired computations or run the computer program. In one embodiment, the functionality of the processor 118 may be limited to tasks performed by the pre-processor module 110. In another embodiment, the functionality of the processor 118 may be limited to the functions performed by the motion signal generator module 112. In another embodiment, the functionality of the processor 118 is limited to the functionality performed by the motion signal analysis module 114. While the processor 118 is shown as a single unit, in exemplary embodiments, the gating system 108 may include at least one processor having the functionality of one or more of the pre-processor module 110, motion signal generator module 112, and the motion signal analysis module 114.

The memory 120 is communicatively coupled to the processor 118 and is configured to be accessed by at least one processor module residing in at least one of the modules 110, 112, and 114. In an exemplary embodiment, the memory 120 may refer to one or more of memory modules. The memory 120 may be a non-transitory storage medium. For example, the memory may be a dynamic random access memory (DRAM) device, a static random access memory (SRAM) device, flash memory or other memory devices. In one embodiment, the memory may include a non-volatile memory or similar permanent storage device, media such as a hard disk drive, a floppy disk drive, a compact disc read only memory (CD-ROM) device, a digital versatile disc read only memory (DVD-ROM) device, a digital versatile disc random access memory (DVD-RAM) device, a digital versatile disc rewritable (DVD-RW) device, a flash memory device, or other non-volatile storage devices. In one specific embodiment, a non-transitory computer readable medium may be encoded with a program to instruct at least one processor to perform functions of one or more of the pre-processor module 110, the motion signal generator module 112, and the motion signal analysis module 114.

In one embodiment, at least one of the pre-processor module 110, the motion signal generator module 112, the motion signal analysis module 114, is stored in the memory module 120 and executable by at least one processor module 118. In those embodiments, the other modules are hardware modules co-operatively interacting with the modules stored in the memory. In some embodiments, at least one of the modules 110, 112, and 114 are located in a different geographic location. In one embodiment, the gating system 108 is integrated in the imaging modality 104. In other embodiments, the gating system 108 is part of the computer display device 126.

Figure 2:
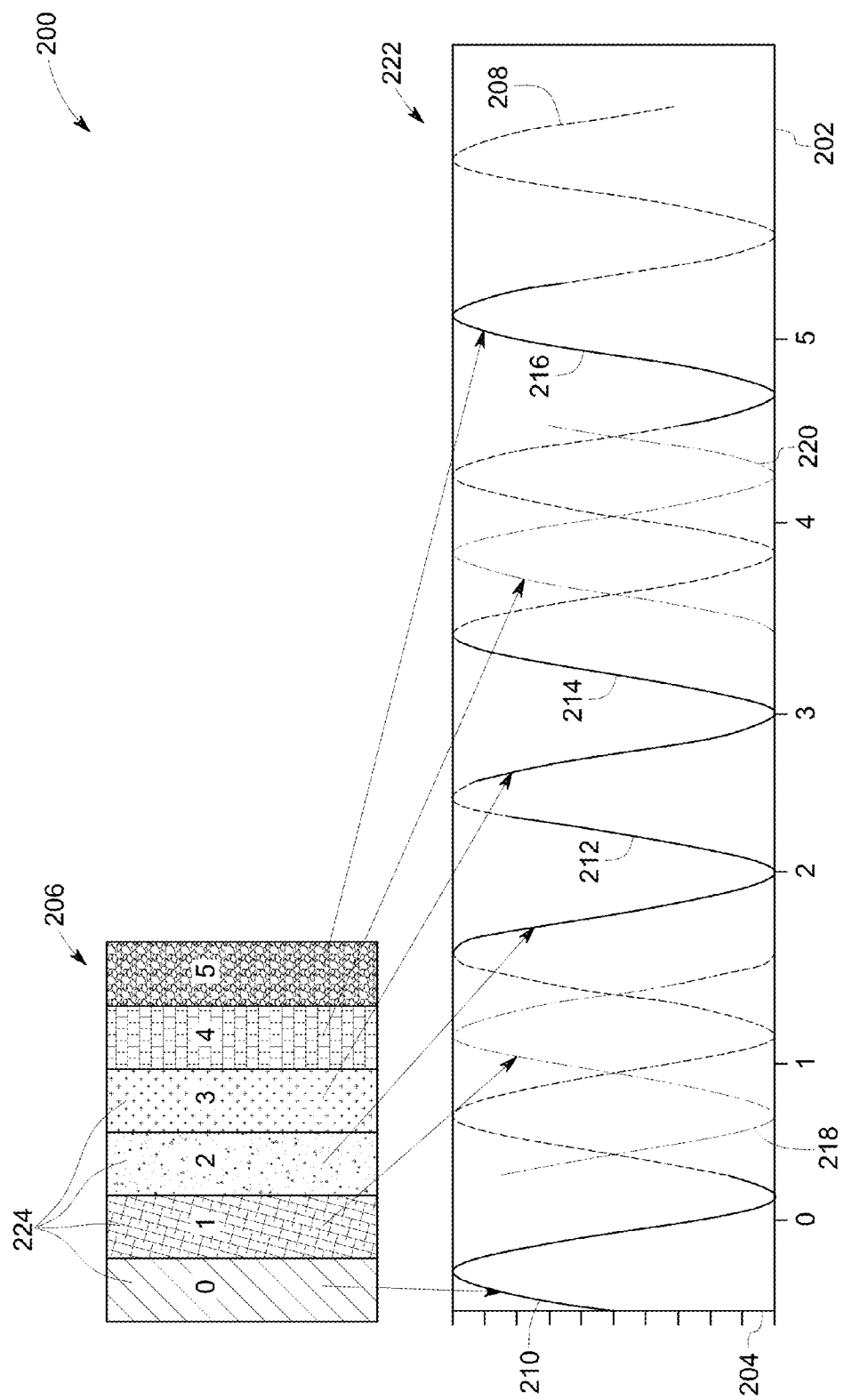
FIG. 2 is a graph of an example of a plurality of signals corresponding to a plurality of bed positions.

FIG. 2 is an illustration 200 including a schematic 206 of a plurality of bed positions and a graph 222 illustrating a plurality of signals corresponding to the plurality of bed positions in accordance with an exemplary embodiment. The schematic 206 represents a plurality of bed positions 224 used for measuring the time-varying image dataset. The graph 222 includes an x-axis 202 representative of time and a y-axis representative of value 204 of the quasi-periodic motion signal of the patient. The graph 222 illustrates a signal 208 represented in dashed line to be derived from the time-varying image dataset acquired from the multiple bed positions 224. The signal 208 may be the respiratory signal or cardiac signal of the patient and is illustrated as a sine wave for convenience of representation. The graph 222 illustrates a plurality of segments of signal 210, 212, 214, 216, 218 and 220 measured from a plurality of bed positions 224. In one embodiment, the plurality of segments may be overlapping at the edges to a different extent.

In one embodiment, the signal 208 is generated based on the plurality of segments 210, 212, 214, 216, 218 and 220. The graph 222 illustrates segments 210, 212, 214, and 216 in phase alignment with the signal 208 and the segments 218, 220 exhibit a phase reversal with respect to the signal 208. The plurality of segments may correspond to the plurality of motion signals corresponding to the motion data of a single bed position. In another embodiment, the plurality of segments correspond to the plurality of bed positions. The polarity of the segments 218 and 220 are reversed and are combined with the other segments 210, 212, 214 and 216 to generate the signal 208.

Figure 3:
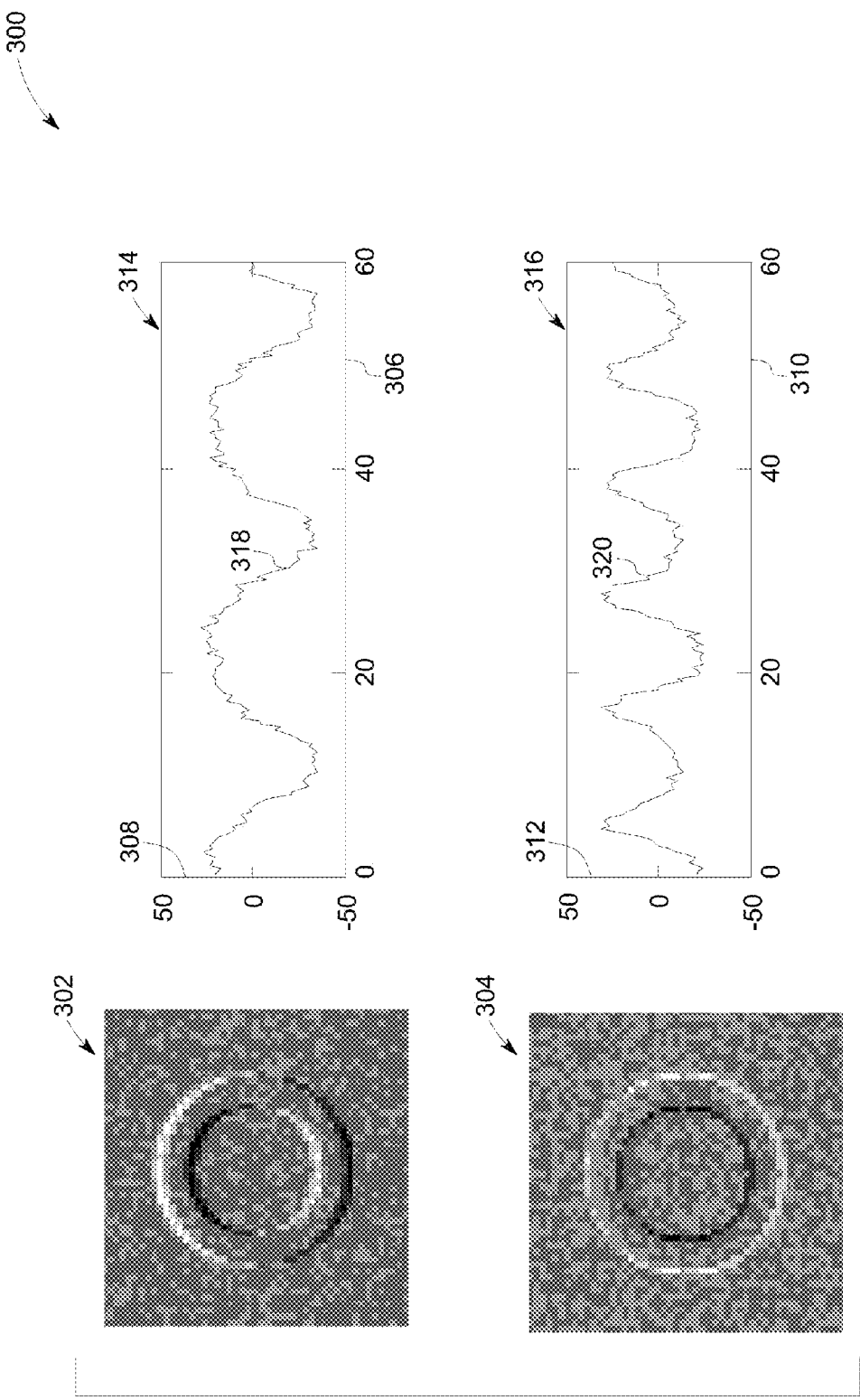
FIG. 3 illustrates examples of a plurality of dataset components and corresponding motion signals.

FIG. 3 illustrates a schematic representation 300 of principal component decomposition of a time-varying image dataset in accordance with an exemplary embodiment. The schematic 300 includes a plurality of dataset components 302, and 304 and a plurality of graphs 314 and 316 of a plurality of motion signals corresponding to the plurality of dataset components 302 and 304. The graph 314 has an x-axis 306 representative of time and a y-axis 308 representative of value. The graph 314 includes a curve 318 representative a first motion signal corresponding to the dataset component 302. The graph 316 includes an x-axis 310 representative of time and a y-axis 312 representative of value. The graph 316 includes a curve 320 representative of a second motion signal corresponding to the dataset component 304. The plurality of motion signals represented by curves 318 and 320 may exhibit a phase reversal due to the phase reversal of the corresponding dataset components. Embodiments of the technique identify and correct such phase reversals and enable generation of a correct gating signal.

The plurality of dataset components $\{V_k \text{ for all } k\}$ is determined by computing principal vectors based on Singular Value Decomposition (SVD) of the plurality of time frame images $\{I(n) \text{ for all } n\}$. The singular value decomposition is given by, $$I(n) \approx \bar{d} + \Sigma_{k=1}^N V_k w_k(n) \quad (1)$$

where, I(n) is the time-varying image dataset, the first term of the Eq (1) is a mean term of the time-varying image dataset I(n), and the second term is a singular value decomposition having N terms with each having a dataset component $V_k$ and a corresponding motion signal $w_k(n)$.

Figure 4:
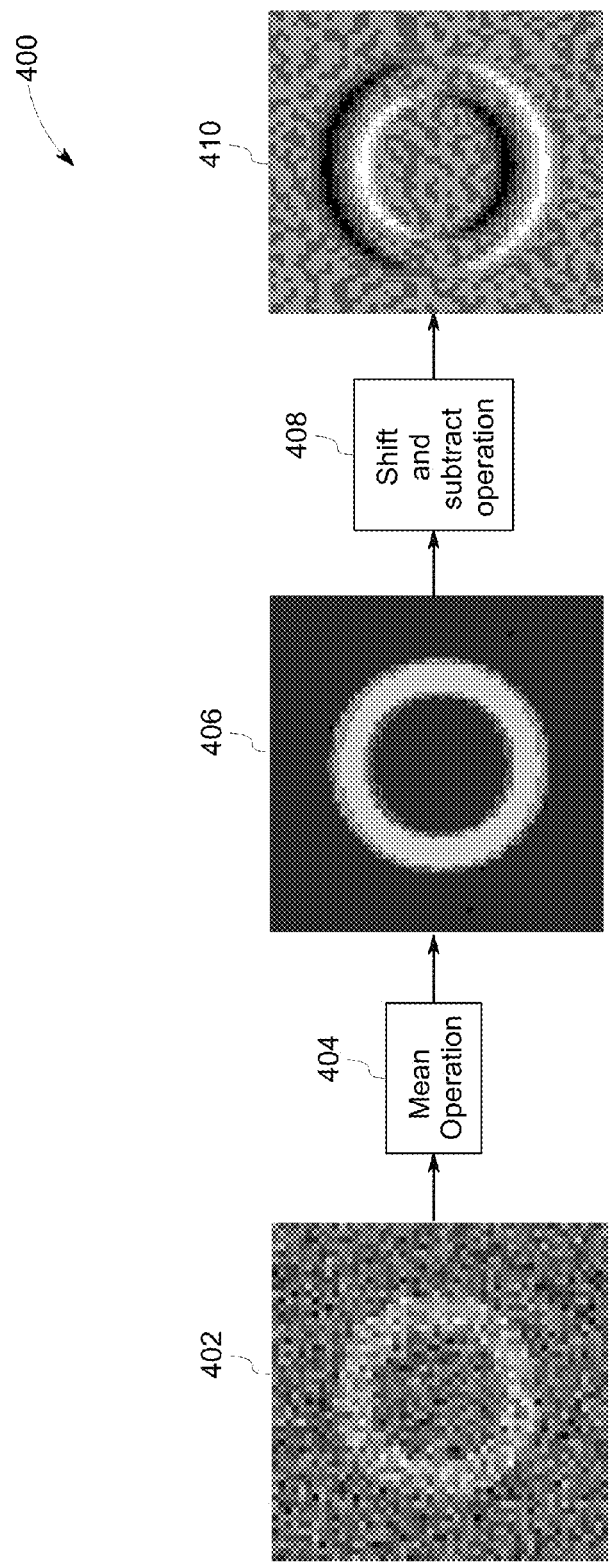
FIG. 4 illustrates an example of a reference data based on the time-varying dataset.

FIG. 4 illustrates a schematic 400 of a reference data based on the mean image and the time-varying image dataset in accordance with an exemplary embodiment. The schematic 400 includes the time-varying image dataset 402 acquired from the imaging modality, a mean image 406 and a reference data 410. The time-varying image dataset 402 includes a plurality of time frames of images. The mean image 406 is determined based on the plurality of images of the time-varying image dataset using a mean operation 404. In one embodiment, the mean operation refers to determining a mean of the plurality of images. The mean image is given by:

$$\bar{I} = \frac{1}{N}\sum_{n=1}^{N} I_n \quad (2)$$

In another embodiment, the mean operation refers to a weighted average of the plurality of images. For better understanding, the input image frame is represented as $I_n \approx I_0(\cdot + v_n)$, where $I_0$ is the base image and $v_n$ is a non-rigid motion applied to $I_0$ resulting in $I_n$. Assuming small deformations of motion in the image $I_0(\cdot + v_n)$, $$I_0 \approx I_0(\cdot + v_n)$$

$$\approx I_0 + \nabla I_0 v_n \quad (3)$$

$$\approx I_0 + u_n \quad (4)$$

where, $\nabla I_0$ is image gradient, $u_n = \nabla I_0 v_n$ is the motion along the image gradient $\nabla I_0$. In some cases, the plurality of images are affected by spatially varying sensitivity patterns, for instance due to varying detection efficiencies. In such an embodiment, these equations have to be modified to take these sensitivities into account.

The reference data 410 is determined based on the mean image 406 of the time-varying image dataset 402 using a shift and subtract operation 408. In one embodiment, a shifted mean image is generated by shifting the mean image 406 in a predetermined direction. A difference between the shifted mean image and the mean image 406 is computed to generate the reference data 410. The reference data generated in this embodiment is referred herein as asymmetrical reference data. In another embodiment, the mean image is shifted in one direction to generate a first shifted image. A second shifted image is generated by shifting the mean image in an opposite direction. A difference of the first shifted image and the second shifted image is determined to generate the reference data. The reference data generated in this embodiment is referred herein as symmetrical reference data. In the present embodiment, the reference data 410 is also referred as 'reference image'. In other embodiments, other signals such as lung density signal may be used as reference data for deriving the polarity of the plurality of motion signals.

Embodiments of the technique use the reference image 410 to identify and correct phase reversal in the plurality of motion signals. In one embodiment, a correlation function between the reference image and each of the plurality of dataset components is computed to determine a plurality of correlation functions. In one specific embodiment, a cross correlation coefficient for the dataset component Vk is computed as:

$$\chi_k = V_k \cdot (\nabla I \cdot v) \quad (5)$$

where, the cross correlation coefficient is the inner product of the dataset component $V_k$ and the corresponding motion v along the image gradient. The motion v is chosen in a pre-defined direction. In one embodiment, the motion v, corresponding to respiratory signal, is a vertical motion. In another embodiment, the motion v, corresponding to cardiac signal, is a radial motion representative of contraction and expansion. In one embodiment, the motion v, corresponding to head movements, is a sideways motion. The Equation (5) is expressed in an alternate form using the symmetric reference data as:

$$\chi_k = V_k \cdot (I(\cdot+v) - I(\cdot-v)) \quad (6)$$

where, $I(\cdot+v_n)$ is mean image shifted in first direction and $I(\cdot-v_n)$ is mean image shifted in a second direction opposite to the first direction. As mentioned in a previous paragraph, in certain embodiments, spatially varying sensitivities need to be taken into account. In one embodiment, the mean image is first corrected for these spatially varying sensitivities by division before Eq. (6) is applied. The amplitude of each of the cross correlation coefficients $\chi_k$ is now compared with zero value. If the amplitude is less than zero value, the phase of the motion signal corresponding to the dataset component is reversed (e.g., multiplied by a minus one). e.g.

if $\chi_k$<0, reverse the phase if $\chi_k$≥0, retain the phase (7)

where, the phase corresponds to the phase of the motion signal $w_k(n)$ corresponding to the principal component Vk. If the amplitude is greater than or equal to zero, the phase of the motion signal is not altered. The plurality of motion signals after phase correction are in phase alignment and are suitable for combining to generate a gating signal. In some embodiments, the amplitude of the cross correlation coefficient is used to determine motion signals corresponding to the quasi-periodic motion data. The magnitude of each of the correlation coefficient is compared with a predetermined threshold. If the magnitude of the correlation coefficient is greater or equal to the predetermined threshold, motion signal corresponding to the correlation coefficient is identified as corresponding to the quasi-periodic motion data. If all correlation coefficients are less than a minimum threshold, the quasi-periodic motion data is considered as insignificant. In such embodiments, gating is not required because the motion artifacts caused by patient motion are not significant.

In some exemplary embodiments applicable to specific imaging modalities such as CT, a lung density signal is used as the reference data for generating the gating signal. A plurality of correlation coefficients are determined by computing cross correlation of the plurality of motion signals with the lung density signal. The polarity of the plurality of dataset components are derived based on the sign of the correlation coefficients. The magnitudes of the correlation coefficients are used to identify one or more motion signals for constructing the gating signal.

In some embodiments, the time-varying image dataset includes overlapping data from adjacent bed positions. In such embodiments, the last slice of one bed position overlaps with a first slice of an adjacent bed position and the two slices are correlated. In some embodiments, the time-varying image dataset does not include overlapping dataset from adjacent bed positions. In such embodiments, extrapolated versions of last few slices of one bed position are correlated with the extrapolated versions of the first few slices of the adjacent bed position. The extrapolated version of a slice is determined using, but not limited to, image intensity based techniques, and motion vector based techniques. In one embodiment, an overlapping region, between a first bed position and a second bed position, among the plurality of bed positions is identified. A first dataset corresponding to the first bed position and a second dataset corresponding to the second bed position are selected in the overlapping region. The correlation between the first dataset and the second dataset may be used to derive polarity of gating signals corresponding to adjacent bed positions. In one exemplary embodiment, cross correlation, between the slices of the first bed position with overlapping slices of the second bed position, is used to derive the polarity of the gating signals. In exemplary embodiments, the cross correlation is determined based on any one or more of time-varying datasets, gated data sets, and transformed datasets. In one exemplary embodiment, cross correlation between a principal component of the first bed position with respective principal component of the second bed position is used to align polarity of the gating signals.

In an alternate embodiment, polarity of the plurality of gating signals are derived by employing a constrained least squares approach in the signal decomposition technique. For example, one or more dataset components of a previous bed position may be used while decomposing the time-varying dataset corresponding to the next bed position.

In some embodiments, the time-varying image dataset includes data from multiple modalities. In such embodiments, the phase correction is performed for signals acquired from each of the multiple modalities. In one example, multimodal dataset includes PET-CT data having image data acquired from PET and CT modalities. A plurality of motion signals are determined for each time-varying image dataset acquired from PET and CT modalities over a few breathing cycles or a few cardiac cycles. The motion signals corresponding to the PET and CT modalities are correlated to perform phase matching of the gating signals of PET and CT data. In another example, multimodal dataset includes PET-MR data having image data acquired simultaneously from PET and MR modalities. The gating signals of image dataset from PET and MR are phase matched using cross correlation of motion signals corresponding to the PET and MR image datasets.

In one embodiment, a first time-varying dataset corresponding to a first imaging modality, and a second time-varying dataset corresponding to a second imaging modality, are considered. A first gating signal corresponding to the first imaging modality and a second gating signal corresponding to the second imaging modality, are determined using the technique outlined in previous paragraphs. The gating signals of first time-varying image dataset and the second time-varying dataset are phase matched based on the sign corrected first gating signal and the second gating signal.

Figure 5:
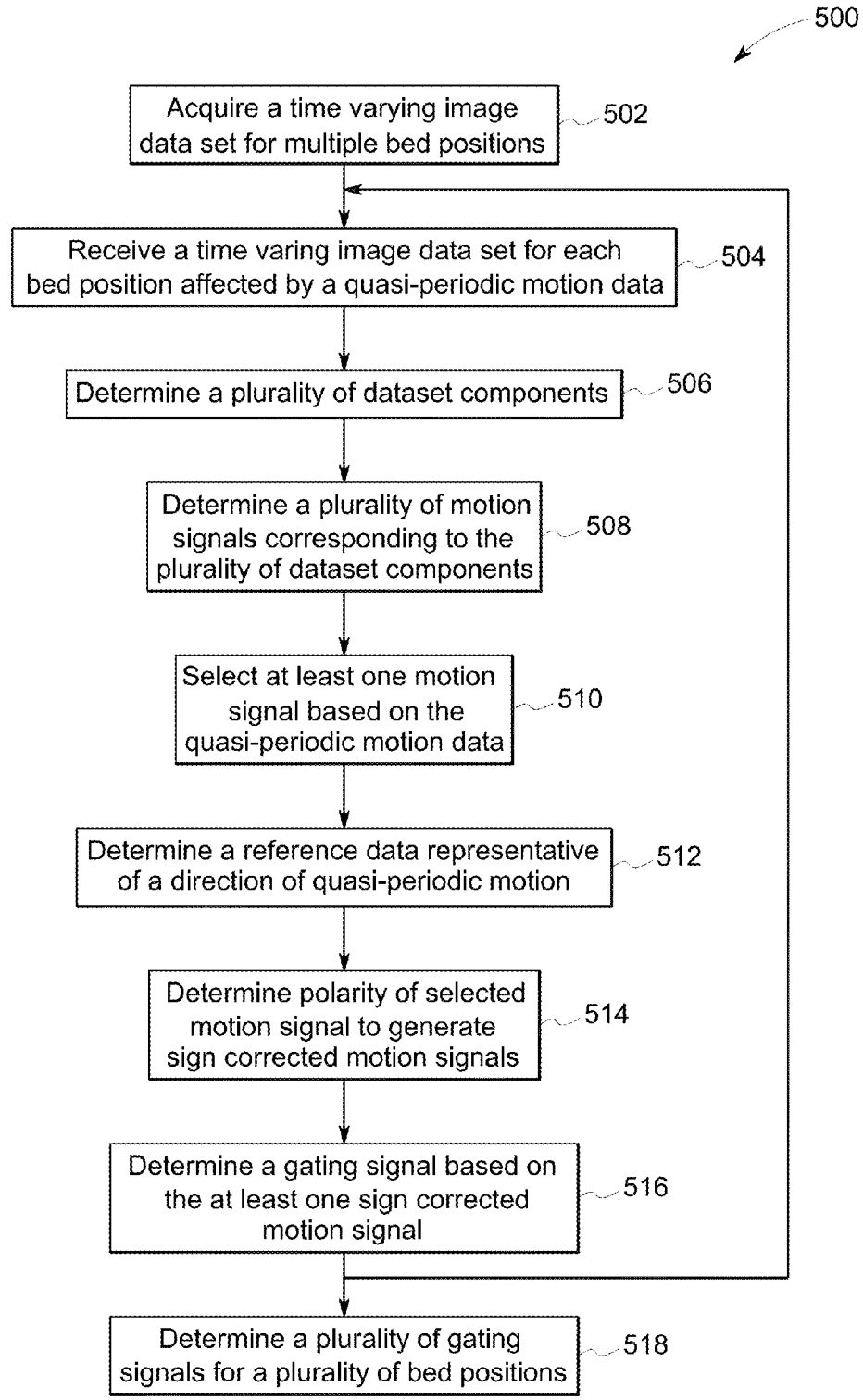
FIG. 5 is a flow chart of an example of a method for determining a gated signal for PET signal acquired from a plurality of bed positions.

FIG. 5 is a flow chart 500 of a method for determining a gated signal for an image dataset acquired from a plurality of bed positions in accordance with an exemplary embodiment. The method in the flow chart 500 generates a gating signal for the time-varying image dataset acquired from a plurality of bed positions. The method acquires a time-varying image dataset from a plurality of bed positions in step 502. In an exemplary embodiment, the time-varying image dataset is generated by a medical imaging modality using techniques such as PET and CT. The method further includes receiving the time-varying image dataset corresponding to a bed position among the plurality of bed positions 504. The time-varying image dataset is affected by quasi-periodic motion data generated due to one or both of respiration activity and cardiac activity of the patient. The method further includes determining a plurality of dataset components corresponding to the dataset 506. In one embodiment, the plurality of dataset components are determined as principal components of the time-varying image dataset. A singular value decomposition of a matrix generated based on the time-varying image dataset corresponding to the bed position is employed to generate one or principal components of the time-varying image dataset. The method further includes determining a plurality of motion signals corresponding to the plurality of dataset components based on the time-varying image dataset 508. The plurality of motion signals are representative of motion in the image.

One or more of the plurality of motion signals are representative of the quasi-periodic motion data affecting the time-varying image dataset.

The method also includes selecting at least one dataset component among the plurality of dataset component among the plurality of dataset components based on the quasi-periodic motion data 510. In one embodiment, known information about the quasi-periodic motion data is used to select at least one motion signal among the plurality of motion signals. As an example, a respiration signal has a frequency component in a range 0.1 Hz to 0.4 Hz. This information may be used to identify one or more plurality of motion signals among the plurality of motion signals. The method includes deriving the polarity of the motion signals. In one embodiment, a reference data is used to determine the polarity of the motion signal 512. The reference data is determined based on a difference between a mean image and a shifted mean image derived from the time-varying image dataset. In one embodiment, the mean image is determined as a mean of the plurality of frames of the time-varying image dataset. Further, determining the shifted image includes shifting the mean image in a predetermined direction. The method of deriving polarity includes determining at least one correlation function based on the shifted image and at least one dataset component. The cross correlation function corresponding to the dataset component is compared with zero value. When the sign value is negative, the phase of the motion signal corresponding to the dataset component is reversed.

The polarity of each of the selected dataset components are derived to generate a plurality of sign corrected motion signals 514. A gating signal is determined by combining one or more of the plurality of sign corrected motion signals 516. In one embodiment, the combining of one or more component signals is through a linear combination operation. A plurality of gating signals are determined based on the time-varying image dataset corresponding to the plurality of bed positions 518. A plurality of gated dataset are generated based on the plurality of gating signals and the plurality of corresponding time-varying image datasets. The plurality of gated datasets generated in this way may be combined readily without any further processing.

Not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

The invention claimed is:

1. A method, comprising:
   receiving a time-varying image dataset corresponding to a bed position, wherein the time-varying image dataset is generated by a medical imaging modality and affected by a quasi-periodic motion data;
   applying a signal decomposition technique to the time-varying image dataset to generate a transformed dataset, wherein the transformed dataset comprises a plurality of dataset components and a plurality of motion signals;
   determining a mean image based on the time-varying image dataset;
   determining a first shifted image by shifting the mean image in a first direction and a second shifted image by shifting the mean image in a second direction opposite to the first direction;
   determining a reference data based on a difference of the first shifted image and the second shifted image;
   deriving a polarity of each of the plurality of motion signals based on the reference data and the plurality of dataset components to generate a plurality of sign corrected motion signals; and
   determining a gating signal corresponding to the bed position based on at least one of the plurality of sign corrected motion signals.

2. The method of claim 1, wherein determining the gating signal comprises generating a plurality of gating signals corresponding to a plurality of image data sets acquired from a plurality of bed positions.

3. The method of claim 2, further comprising:
   identifying an overlapping region between a first bed position and a second bed position among the plurality of bed positions;
   selecting a first dataset corresponding to the first bed position and a second dataset corresponding to the second bed position in the overlapping region; and
   deriving a polarity of the gating signals corresponding to the first bed position and the second bed position based on a correlation between the first dataset and the second dataset.

4. The method of claim 3, further comprising:
   generating a plurality of gated image datasets based on the plurality of image datasets and corresponding plurality of gating signals; and
   generating a combined dataset based on the plurality of gated image datasets corresponding to the plurality of bed positions.

5. The method of claim 1, wherein determining the gating signal comprises:
   determining a first gating signal for a first time-varying image dataset corresponding to a first medical imaging modality and a second gating signal for a second time-varying image dataset corresponding to a second imaging modality; and
   phase matching the first gating signal and the second gating signal based on a cross correlation of the plurality of motion signals corresponding to the first time-varying image dataset and the second time-varying image dataset.

6. The method of claim 1, wherein the motion data comprises at least one of a respiratory motion and a cardiac motion.

7. The method of claim 1, wherein applying the signal decomposition technique comprises:

performing a principal component analysis of the time-varying image dataset to generate a plurality of principal components; and projecting the time-varying image dataset on to the plurality of principal components of the image dataset to determine the plurality of motion signals.

8. The method of claim 1, wherein the deriving the polarity comprises:
determining a correlation value based on a cross correlation of the reference data with a dataset component among the plurality of dataset components; and
determining the polarity based on a sign of the correlation value.

9. A system, comprising:
at least one processor module and a memory module communicatively coupled to a communications bus;
a pre-processor module that receives a time-varying image dataset corresponding to a bed position, wherein the time-varying image dataset is generated by a medical imaging modality and affected by a quasi-periodic motion data;
a motion signal generator module, communicatively coupled to the pre-processor module, that performs signal decomposition of the time-varying image dataset and generates a transformed dataset, wherein the transformed dataset comprises a plurality of dataset components and a plurality of motion signals;
a motion signal analysis module, communicatively coupled to the motion signal generator module, that:
determines a mean image based on the time-varying image dataset;
determines a first shifted image by shifting the mean image in a first direction and a second shifted image by shifting the mean image in a second direction opposite to the first direction;
determines a reference data based on a difference of the first shifted image and the second shifted image;
derives a polarity of each of the plurality of motion signals based on the reference data and the plurality of dataset components to generate a plurality of sign corrected motion signals; and
determines a gating signal corresponding to the bed position based on the at least one of the plurality of sign corrected motion signals;
wherein, at least one of the pre-processing module, the motion signal generator module, and the motion signal analysis module are stored in the memory module and executable by the processor module.

10. The system of claim 9, wherein the motion signal analysis module further generates a plurality of gating signals corresponding to a plurality of bed positions.

11. The system of claim 10, wherein the motion signal analysis module further:
identifies an overlapping region between a first bed position and a second bed position among the plurality of bed positions;
selects a first dataset corresponding to the first bed position and a second dataset corresponding to the second bed position in the overlapping region; and
derives a polarity of the gating signal corresponding to the first bed position and the second bed position based on a correlation between the first dataset and the second dataset.

12. The system of claim 11, wherein the motion signal analysis module further:
generates a plurality of gated image datasets based on the plurality of image datasets and corresponding the plurality of gating signals; and
generates a combined dataset based on the plurality of gated image datasets corresponding to the plurality of bed positions.

13. The system of claim 10, wherein the motion signal analysis module:
determines a first gating signal for a first time-varying image dataset corresponding to a first medical imaging modality and a second gating signal for a second time-varying image dataset corresponding to a second imaging modality; and
performs phase matching of the first gating signal and the second gating signal based on a cross correlation of the plurality of motion signals corresponding to the first time-varying image dataset and the second time-varying image dataset.

14. The system of claim 10, wherein the motion signal analysis module:
determines a plurality of principal components of the time-varying image dataset; and
projects the time-varying image dataset on to the plurality of principal components to determine the plurality of motion signals.

15. The system of claim 10, wherein the motion signal analysis module:
determines a correlation value based on cross correlation of the reference data with a dataset component among the plurality of dataset components; and
determines the polarity based on a sign of the correlation value.

16. A non-transitory computer readable medium having instructions causing at least one processor module to:
receive time-varying image dataset corresponding to a bed position, wherein the time-varying image dataset is generated by a medical imaging modality and affected by quasi-periodic motion data;
apply a signal decomposition technique to the time-varying image dataset to generate a transformed dataset, wherein the transformed dataset comprises a plurality of dataset components and a plurality of motion signals;
determine a mean image based on the time-varying image dataset;
determine a first shifted image by shifting the mean image in a first direction and a second shifted image by shifting the mean image in a second direction opposite to the first direction;
determine a reference data based on a difference of the first shifted image and the second shifted image;
derive a polarity of each of the plurality of motion signals based on the reference data and the plurality of dataset components to generate a plurality of sign corrected motion signals; and
determine a gating signal corresponding to the bed position based on at least one of the plurality of sign corrected motion signals.

* * * * *